United States Patent
Thommandram et al.

(10) Patent No.: US 11,058,352 B2
(45) Date of Patent: Jul. 13, 2021

(54) ELECTRICAL STIMULATION FACILITATED SYMPTOM TRANSFERENCE FOR EMPATHIC RESPONSE

(71) Applicant: KLICK INC., Toronto (CA)

(72) Inventors: Anirudh Thommandram, Toronto (CA); Yan Fossat, Toronto (CA)

(73) Assignee: Klick Inc., Toronto (CA)

( * ) Notice: Subject to any disclaimer, the term of this patent is extended or adjusted under 35 U.S.C. 154(b) by 313 days.

(21) Appl. No.: 16/192,194

(22) Filed: Nov. 15, 2018

(65) Prior Publication Data

US 2019/0142339 A1    May 16, 2019

Related U.S. Application Data

(60) Provisional application No. 62/587,266, filed on Nov. 16, 2017.

(51) Int. Cl.
*A61B 5/00* (2006.01)
*A61B 5/11* (2006.01)
*A61N 1/04* (2006.01)
*A61N 1/36* (2006.01)
(Continued)

(52) U.S. Cl.
CPC .......... *A61B 5/4884* (2013.01); *A61B 5/0077* (2013.01); *A61B 5/1101* (2013.01); *A61B 5/1128* (2013.01); *A61B 5/389* (2021.01); *A61B 5/4082* (2013.01); *A61N 1/0452* (2013.01); *A61N 1/36003* (2013.01); *A61B 2562/0219* (2013.01); *A61N 1/0476* (2013.01); *A61N 1/0484* (2013.01); *G06F 3/011* (2013.01); *G06F 3/014* (2013.01); *G06F 3/015* (2013.01)

(58) Field of Classification Search
CPC ... A61B 5/4884; A61B 5/0077; A61B 5/0488; A61B 5/1101; A61B 5/1125; A61B 5/4082; A61B 2562/0219; A61N 1/0452; A61N 1/36003; A61N 1/0476; A61N 1/0484; G06F 3/011; G06F 3/014; G06F 3/015
See application file for complete search history.

(56) References Cited

U.S. PATENT DOCUMENTS 6,341,237 B1 * 1/2002 Hurtado ............. A61N 1/36014
607/148
9,545,514 B2 * 1/2017 Minogue .............. A61N 1/0484

OTHER PUBLICATIONS

Ho, A. J., Turnbull, J., & Fossat, Y. (2017). Compassion through tele-empathy: technology-mediated symptom transference. Future healthcare journal, 4(3), 219-220. https://doi.org/10.7861/futurehosp.4-3-219 (Year: 2017).*

(Continued)

*Primary Examiner* — Sean P Dougherty
*Assistant Examiner* — Kyle W. Kretzer
(74) *Attorney, Agent, or Firm* — Bereskin & Parr LLP/S.E.N.C.R.L., s.r.l.; I. Laurence MacPhie

(57) ABSTRACT

A method of simulating a tremor in a subject and evoking an empathetic response in the subject towards a patient suffering from tremors, the method comprising: synthesizing a tremor inducing signal, which may be done by capturing and analyzing EMG measures of electrical pulses derived from a sensed neuromuscular event associated with tremors experienced by a patient; and applying an electrical muscle stimulation to the subject using the synthesized pulses associated with the patient experiencing tremors.

6 Claims, 5 Drawing Sheets

(51) Int. Cl.
  *A61B 5/389* (2021.01)
  *G06F 3/01* (2006.01)

(56) References Cited

OTHER PUBLICATIONS

Grimaldi, G.; Manto, M. Neurological Tremor: Sensors, Signal Processing and Emerging Applications. Sensors 2010, 10, 1399-1422. (Year: 2010).*
Klick labs debuts first device to record and transmit parkinson's tremors; highlights link between clinical empathy and improved patient outcomes. (Apr. 24, 2017). Business Wire (Year: 2017).*
Dixon, Guy, "The feeling of empathy", Aug. 24, 2017, The Globe and Mail (Year: 2017).*
Jauhar, Sandeep, "Empathy Gadgets", Jul. 29, 2017, The New York Times (Year: 2017).*
Rahhal, Natalie, "Man feels his twin brother's early onset Parkinson's tremors thanks to 'tele-empathy' device that Simulates his muscle spasms", Nov. 20, 2017, dailymail.com (Year: 2017).*
Hay, Susan, "Toronto organization introduces device to help better understand Parkinson's disease", May 1, 2017, Global News (Year: 2017).*
Crotti, Nancy, "Do caregivers need a Parkinson's disease simulation device to experience empathy?", Apr. 26, 2017, MedCity News (Year: 2017).*
Snyder Bulik, Beth, "Empathy matters: Klick Labs device simulates Parkinson's tremors, directly", Apr. 24, 2017, Fierce Pharma (Year: 2017).*
Farr, Christina, "This device will let you feel what it's like to suffer from Parkinson's", Nov. 9, 2017, CNBC (Year: 2017).*
Klick Labs debuts first device to transmit tremors, Youtube. (May 14, 2018). Retrieved from https://www.youtube.com/watch?v=d-sfG5pV-tM&feature=emb_logo (Year: 2018).*
Immel, SR, Kiff, RE, Armstrong, JL, & Stone, RB. "A Physical Hand Tremor Simulator for Use With Inclusive Design Research." Proceedings of the ASME 2014 International Mechanical Engineering Congress and Exposition. vol. 11: Systems, Design, and Complexity. Montreal, Quebec, Canada. Nov. 20, 2014 (Year: 2014).*
Hess, C. W., & Pullman, S. L. (2012). Tremor: clinical phenomenology and assessment techniques. Tremor and other hyperkinetic movements (New York, N.Y.), 2, tre-02-65-365-1. https://doi.org/10.7916/D8WM1C41 (Year: 2012).*
Ceurstemont, Sandrine, "What it's like to have Parkinson's for 15 minutes", Nov. 19, 2014, NewScientist (Year: 2014).*
Body illusion lets you experience Parkinson's, YouTube. (Nov. 19, 2014). Retried from https://www.youtube.com/watch?v=KUEXAqV9eP4&feature=emb_logo (Year: 2014).*
Habermann, Ryan, "Parkinson's Disease Simulation Design + Build: Empathy Projects", Mar. 26, 2016, NuVu (Year: 2016).*
Produkt + Projekt Wolfgang Moll. (2016). Simulating the senile tremor (Year: 2016).*
Neumann, M., et al., "Physician empathy: definition, outcome-relevance and its measurement in patient care and medical education." GMS Z Med Ausbild, 2012, 29(1), pp. 1-21.
Halpem, J., "Empathy and patient-physician conflicts." J Gen Intern Med, 2007, 22(5), pp. 696-700.
Deladisma, A.M., et al., "Do medical students respond empathetically to a virtual patient?" Am J Surg, 2007, 193, pp. 756-760.
Berry, P., "From Detached Concern to Empathy: Humanizing Medical Practice". BMJ: British Medical Journal., 2001, 323 (7325): 1373. doi:10.1136/bmj.323.7325.1373. ISSN 0959-8138. PMC 1121833.
Riess, H., et al., "Empathy Training for Resident Physicians: A Randomized Controlled Trial of a Neuroscience-Informed Curriculum." Journal of General Internal Medicine, 2012, 27 (10), pp. 1280-1286. doi:10.1007/s11606-012-2063-z. ISSN 0884-8734. PMC 3445669. PMID 22549298.
Palanica, A., et al., "Eliciting clinical empathy via transmission of patient-specific symptoms of Parkinson's disease." Cogent Psychology, 2018, 5(1): 1526459. doi:10.1080/23311908.2018.1526459.
Ho, A.J., et al., "Compassion through tele-empathy: technology-mediated symptom transference." Future Healthcare Journal, 2017, vol. 4, No. 3., pp. 219-220.

* cited by examiner

ELECTRICAL STIMULATION FACILITATED SYMPTOM TRANSFERENCE FOR EMPATHIC RESPONSE

FIELD OF THE INVENTION

The present invention is directed to a device to evoke an empathetic response in a subject. The present invention is directed to a method of using electrical muscle stimulation to evoke empathy.

BACKGROUND OF THE INVENTION

Empathy is defined as the ability to understand and share the feelings of another. Clinical empathy, in particular, can be described as the ability to understand a patient's circumstances, thoughts and feelings, verifying those with the patient, and responding both appropriately and helpfully to the patient. There may be many benefits to empathy among patients, physicians and caregivers. Empathy towards patients has been shown to increase diagnostic accuracy, improved adherence to medical recommendations and better outcomes. A caregiver's appreciation for the patient and their emotional situation can lead to a shared understanding of the patient's response to illness.

Improving empathy towards patients or a disease has traditionally involved narrative techniques such as verbally describing symptoms, testimonials from patients about their experiences or by watching videos of patients' experiences. Recently, technologies such as virtual reality have been employed to make for richer and more immersive viewing experiences. These methods can work well for some situations but for diseases such as Parkinson's disease (PD) or other movement disorders, where there may be apparent motor symptom issues, simple narrative techniques may fall short. Therefore there may be a need for a deeper form of communication to help caregivers be empathetic to patients.

SUMMARY OF THE INVENTION

The aim of the present invention is to provide a method of simulating a tremor in a subject and evoking an empathetic response in the subject towards a patient suffering from tremors, the method comprising: capturing and analyzing the pulses derived from a sensed neuromuscular event associated with tremors experienced by a patient; and applying an electrical muscle stimulation to the subject to mimic the neuromuscular event derived from the sensed information associated with a patient experiencing tremors.

BRIEF DESCRIPTION OF THE DRAWINGS

Referring to the drawings wherein like reference numerals indicate similar parts throughout the several views, several aspects of the present invention are illustrated by way of example, and not by way of limitation, in detail in the figures, wherein.

DESCRIPTION OF VARIOUS EMBODIMENTS

Figure 1:
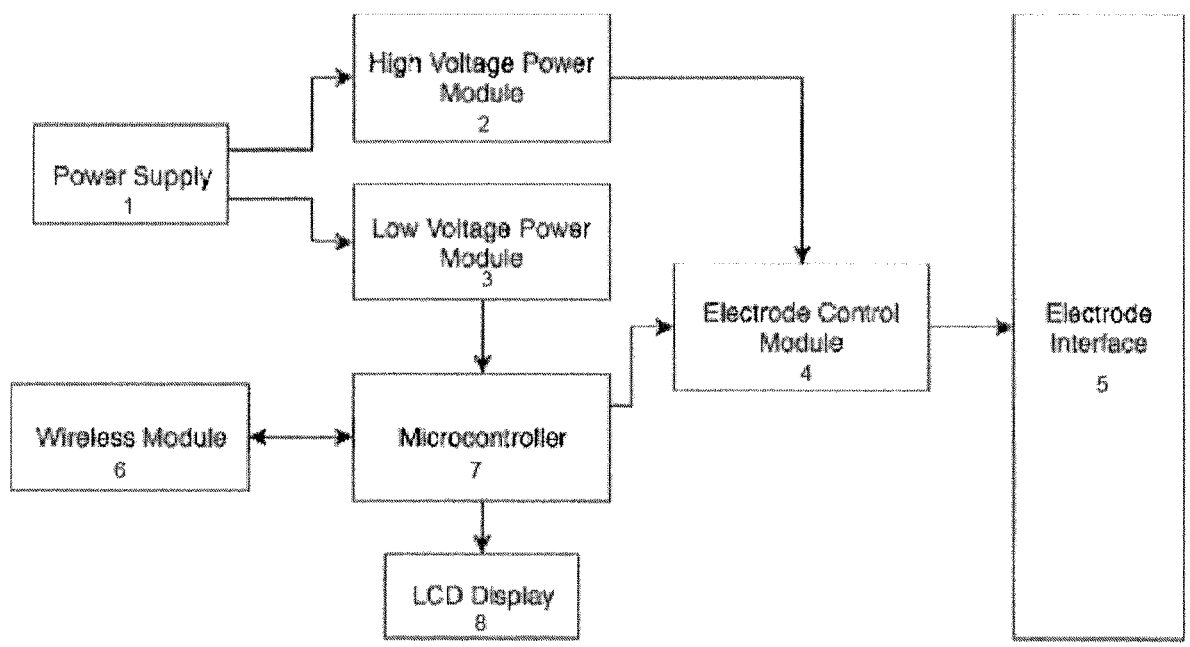
FIG. 1 represents the components of the EMS technology.

The detailed description set forth below in connection with the appended drawings is intended as a description of various embodiments of the present invention and is not intended to represent the only embodiments contemplated by the inventor. The detailed description includes specific details for the purpose of providing a comprehensive understanding of the present invention. However, it will be apparent to those skilled in the art that the present invention may be practiced without these specific details.

The present invention provides a method of simulating a tremor in a subject and evoking an empathetic response in the subject towards a patient suffering from tremors, the method comprising: synthesizing a tremor inducing signal, which may be done by capturing and analyzing the pulses derived from a sensed neuromuscular event associated with tremors experienced by a patient; and applying an electrical muscle stimulation to the subject using the synthesized pulses associated with a patient experiencing tremors.

Tremors are an involuntary, rhythmic muscle contraction leading to shaking movements in one or more parts of the body. It may be a common movement disorder that most often affects the hands but can also occur in the arms, head, vocal cords, torso, and legs. Tremors may be intermittent (occurring at separate times, with breaks) or constant. Tremors can occur sporadically (on their own) or happen as a result of another disorder or trigger. Generally, tremor is caused by a problem in the deep parts of the brain that control movements. Most types of tremor have no known cause, although there are some forms that appear to be inherited. Tremor can occur on its own or be a symptom associated with a number of neurological disorders, including for example: multiple sclerosis, stroke, traumatic brain injury or neurodegenerative diseases that affect parts of the brain (for example, Parkinson's disease). Some other known causes can include: the use of certain medicines (particular asthma medication, amphetamines, caffeine, corticosteroids, and drugs used for certain psychiatric and neurological disorders), alcohol abuse or withdrawal, mercury poisoning, overactive thyroid, liver or kidney failure or anxiety or panic.

Treating tremors can be difficult and patients suffering from tremors may sometime feel that health care practitioners don't understand their disease. The claimed invention may help such practitioners understand what it feels like to experience tremors so that they may be empathetic towards their patient. Empathy towards patients has been shown in literature to have a beneficial impact on the treatment of the patient experiencing tremors for example in diagnostic accuracy and adherence to medical recommendations, for example in Neumann M, Scheffer C, Tauschel D et al. *Physician empathy: definition, outcome-relevance and its measurement in patient care and medical education*. GMS Z Med Ausbild 2012; 29: Doc11; Halpern J. *Empathy and patient-physician conflicts*. J Gen Intern Med 2007; 22: 696-700; and Deladisma A M, Cohen M, Stevens A et al. *Do medical students respond empathetically to a virtual patient?* Am J Surg 2007; 193: 756-760.

The present invention provides a method of simulating a tremor in a subject, which may include capturing and analyzing the pulses derived from a sensed neuromuscular event associated with tremors experienced by a patient. There are at least three ways of obtaining muscle motion data, analyzing it, and generating useful signals associated with a patient suffering from tremors or PD to evoke simulated similar tremor with the help of electrical muscle stimulation (EMS) in another person for the purpose of evoking an empathic response. One method includes generating an electromyogram (EMG). An EMG shows the electrical activity of muscles. This is a preferred method as it provides a direct channel to the desired data to be analysed, namely the activity of the targeted muscles during tremor, and it aligns with the method of stimulation, using EMS with "playback" of the EMG information.

A second method includes taking a video of the muscle motions that may then be analysed using computer vision techniques to determine which muscles need to be stimulated in which order and at which timing and intensity. A third way includes using accelerometers and gyroscope sensors. These sensors have become ubiquitous in wearables such as the Fitbit™ and sophisticated algorithms have been developed for the fusion of data to produce accurate analysis of motions, which can in turn be used to synthesize a tremor-inducing signal.

In an embodiment, the present invention provides a method of simulating a tremor in a subject comprising applying a synthesized electrical muscle stimulation signal to the subject to cause a mimicking of sensed neuromuscular events associated with a patient experiencing tremors. FIG. 1 shows the components of the device that generates and supplies a subject with EMS.

EMS has been traditionally used in sports medicine, physical therapy, for aesthetic and fitness promoting purposes. EMS works by applying electrical current to muscle nerves through electrodes placed on the skin in proximity to the targeted muscles to cause muscle contractions.

The power supply 1 provides a power source to the processor, display, wireless module 6 and the muscle stimulation drive circuitry. It can be regular alkaline batteries such as AA, AAA or rechargeable lithium-ion batteries. In one embodiment, it is a regular 9V PP3-size alkaline battery.

The high voltage power module 2 boosts the battery voltage to that needed for electrical muscle stimulation. EMS may require voltages from 30V to 80V depending on activation intensity and location of muscle stimulation. Areas on the body with larger muscles will require higher voltages. A variable voltage of 30-42V may be used for precise and comfortable activation of muscles in the forearm.

The low voltage power module 3 regulates the battery voltage to provide a stable energy source for the main processor, wireless module, display, and electrode control circuitry.

The wireless module 6 enables the device to receive muscle activity information in real-time, whether it be raw EMG data or a post-analysis or synthesized muscle control signal. It may also enable the device to receive control and communication signals from a connected device such as a smartphone. The module 6 may receive muscle control signals from a smartphone application that analyses streaming EMG data in near real-time to provide a mirrored synthetic tremor.

The microcontroller 7 is the main processor that is used for analysing raw EMG data and generating synthesized muscle control signals. It also has memory and is capable of storing pre-recorded muscle control signal sequences. Muscle control signals consist of impulse timing and intensity specifications.

The electrode control module 4 receives muscle control signals from the processor and has electronic components and circuitry to supply the electrode interface 5 with the required current impulse and voltage to cause desired muscle motions. The module may include components and drive circuits for control over more than one electrode. The module 4 may in one embodiment control 8 or more channels of electrical stimulation and may be connected to a common processor.

The electrode interface 5 can consist of any number of electrodes arranged in a variety of formations. The electrodes can be integrated into garments for different parts of the body to provide stimulation to specific muscles. In one embodiment, 8 or more pairs of electrodes may be integrated into a garment that is strapped to a subject's forearm such that the electrode pairs span the circumference of the forearm targeting the muscles that control hand motion.

In one embodiment the EMS stimulation used for targeting a subject's forearm may be by a DC-DC converter that may boost the battery voltage of 9V to a range of 10V to 38V. The current may be within the range of 50 mA to a 500 Ohm. In one embodiment, the voltage may not vary pulse to pulse but may depend on a subject's body composition to provide a safe stimulation. Other higher voltage ranges may be used for larger muscles such as those in the legs.

Certain parameters that may characterize the pulse stimulation include, for example: pulse intensity, the pulse width, the number of pulses, the pulse frequency and the duration of a synthesized pulse. The pulses that may be used in a subject's forearm may include monophasic pulsed galvanic DC, these pulses may comprise of duration ranges from 10-1000 microseconds. The pulse frequency may range up to 100 Hz. Longer pulse durations may cause greater contractions, however there may be a certain threshold after which contractions may not increase. In such cases a specific sequence of pulses may be used to stimulate stronger contractions, such as limiting the time in between pulses. For example, a pulse interval of 10 ms may not allow the muscle fibres enough time to recover from the previous stimulation thereby providing stronger contractions by in essence compounding the effects of successive closely timed pulses.

Figure 3:
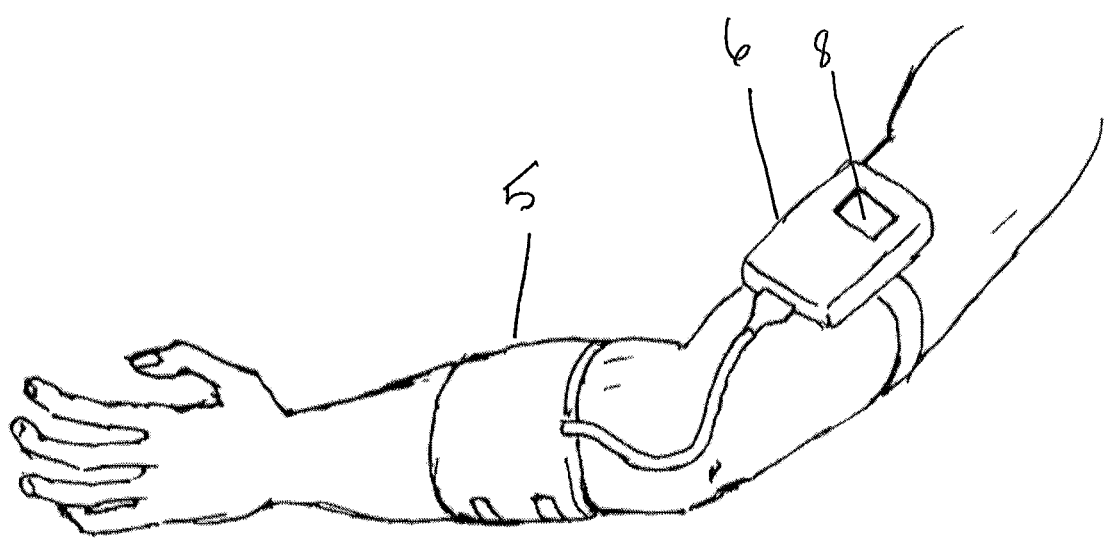
FIG. 3 represents a device in a garment placed on a subject's forearm.
Figure 4:
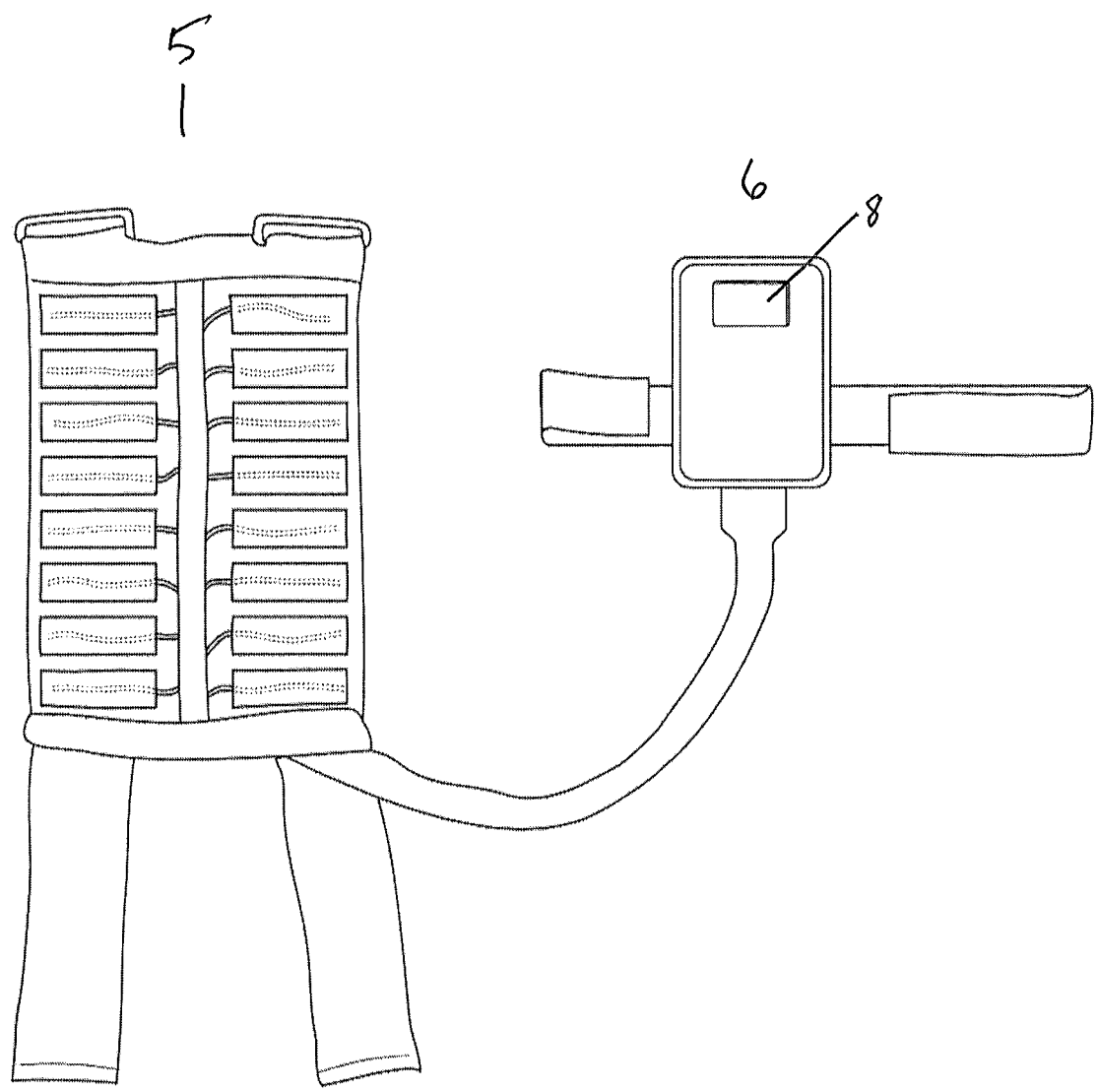
FIG. 4 represents the components of the device in a garment.

When the subject's skin receives the electrical stimulation current via electrodes, muscles near the electrodes contract and relax, producing a motion in the hand and forearm that may be characteristic of or very similar to a Parkinson's tremor. The electrodes may be placed on the subject using technology known in the art, for example using a garment 5. Depending on the muscle to be targeted and the kind of tremor to be stimulated, the design, number of electrodes and channels may vary. As in FIG. 4 the design of the garment may comprise of at least 8 or more channels of stimulation arranged along the circumference of the subject's forearm thereby including at least 16 or more electrodes. FIG. 3 shows the garment on a subject's forearm.

Example

Figure 2:
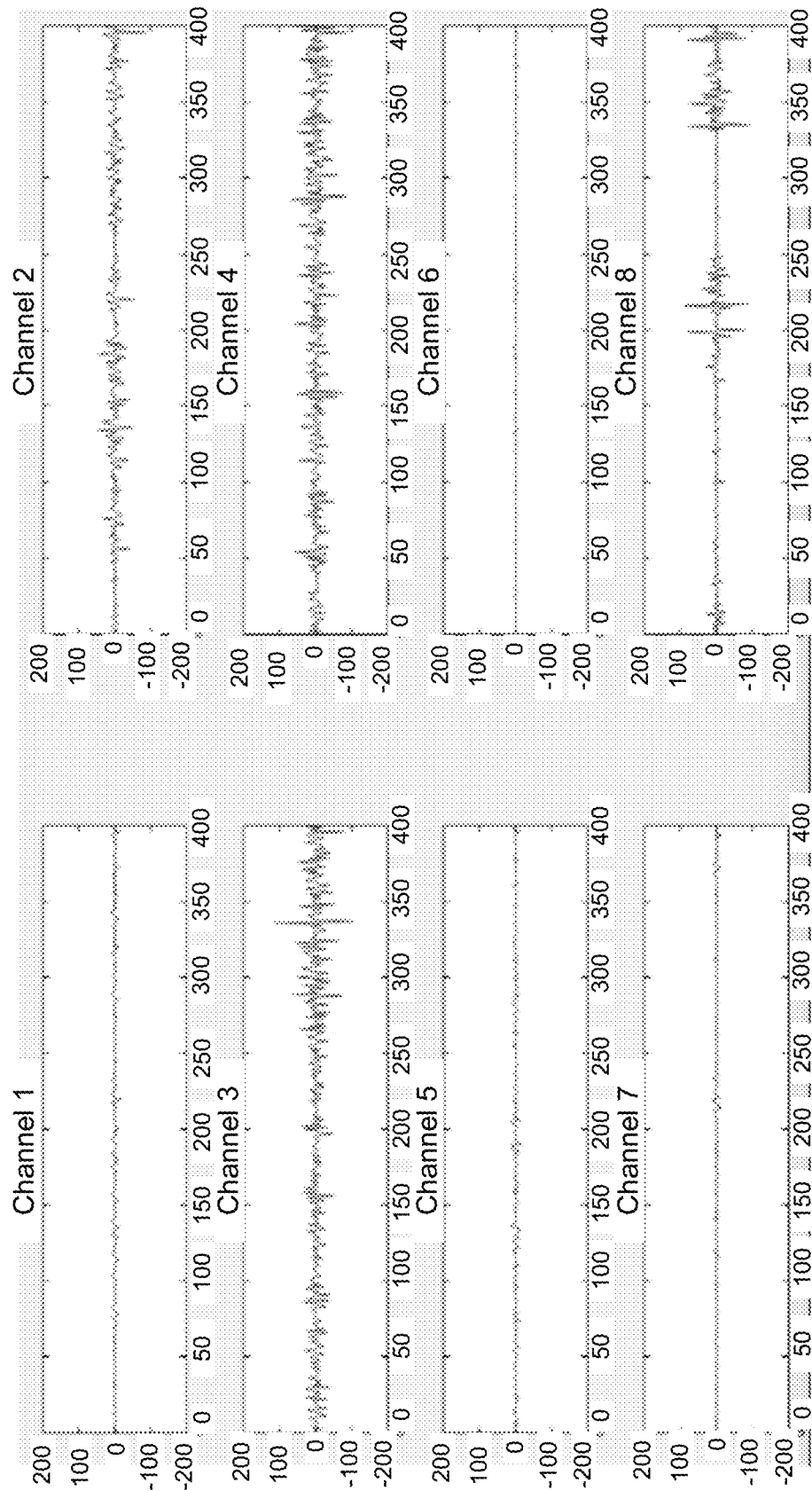
FIG. 2 represents a sample EMG output result.

An EMG capturing device known as the Myo was used to capture and analyse pulses derived from sensed neuromuscular event associated with tremors experienced by a Parkinson's patient. An 8-channel EMG armband was used on a patient's forearm as in FIG. 4. The provided raw EMG data was observed as an integer between −128 and +128 at 200 Hz. FIG. 2 shows the raw data obtained from the EMG.

Figure 5:
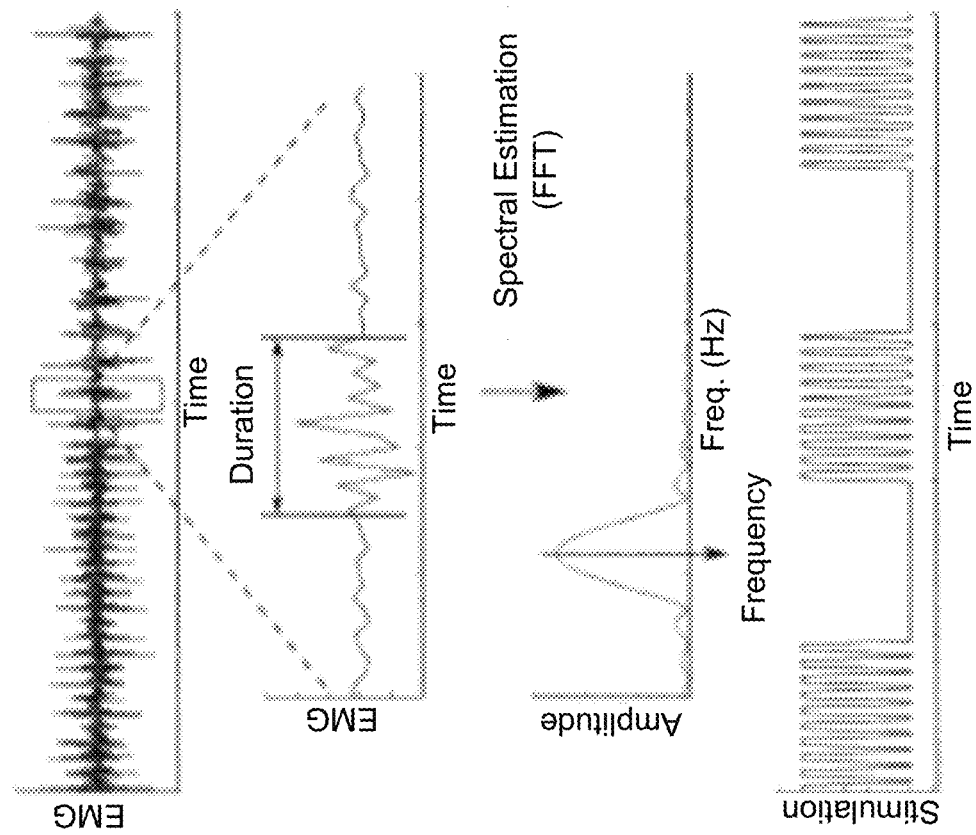
FIG. 5 represents a progressive series of waveforms from a sensed neuromuscular event through several phases of processing to a sample generated pulse train for application to a subject.

Referring to FIG. 5 the raw EMG data was first rectified by converting the raw EMG signal 10 to a positive set of values using the baseline, referred to as the pulse segmentation 12. Areas in the EMG where non-baseline activity was detected, the segment of the signal representing one pulse was isolated for further analysis. Once the segmentation was performed, the EMG data underwent an envelope detection operation to determine the coarse shape of the waveform of the signal. This allowed for differentiating between a short burst contraction and a sustained contraction. A Fourier Transform calculation was then performed to determine the fundamental frequency of the pulse. The duration of the impulse and intensity were also determined, this process is also known as tremor characterization 13. The pulse duration is calculated by performing a threshold filter over a windowed segment of rectified EMG data. The synthesized pulse parameters were calculated using the following equations:

$$t_{off}=((\mathit{Off}_{max}-\mathit{Off}_{min})*((i_{analysed}-0.5)/0.5))+\mathit{Off}_{min}$$

$$n_{iterations}=\min[\max[dur/(t_{off}+t_{on}/1000),1],25]$$

By measuring several periods of the tremor cycle, an average set of impulse parameters can be extracted and an impulse train synthesized consisting of several timed synthesized pulses.

This information from the patient determined the EMS pulse generation, 14, such as for example the pulse intensity, the voltage, the pulse width, the number of pulses, the pulse frequency and the duration of a synthesized pulse administered to a subject to evoke empathy.

Self-reports were used to measure empathy, using a set of questionnaires. Both trait and state empathy were measured to examine dispositional empathy (i.e., how one generally feels on a regular basis) and situational empathy (i.e., how one feels in the moment), respectively. Trait empathy was measured using the Jefferson Scale of Physician Empathy (JSPE; Hojat et al., 2001), which contains 20 items, each answered on a 7-point Likert scale (1="Strongly Disagree", and 7="Strongly agree"). State empathy was measured using a modified version of the State Empathy Scale (adapted from Shen, 2010), which is a 12-item questionnaire, measuring affective, cognitive, and associative components of situational empathy, on 5-point Likert scales anchored at both poles (0="Not at all," and 4="Completely").

Subjects first answered the Jefferson Scale of Physician Empathy to assess overall trait empathy. Next, the subjects were outfitted with the device on their dominant arm and stimulated with a 2-minute tremor simulation from a Parkinson's disease patient. The participant was then asked to perform specific motor function tasks, including buttoning a shirt, and writing their name on a sheet of paper. After the motor function tasks, the participants answered the Modified State Empathy Scale.

The findings showed that use of the device did increase the empathy experienced for the disease by a fairly significant amount.

What is claimed is:

1. A method of simulating a tremor in a subject and evoking an empathetic response in the subject towards a patient suffering from tremors, the method comprising:
    administering an electrical muscle stimulation in a synthesized pattern to the subject to cause tremors in the subject, wherein the synthesized pattern is based on electromyogram (EMG) muscle motion data from a sensed neuromuscular event associated with tremors experienced by the patient,
    wherein the electrical muscle stimulation in the synthesized pattern is administered to the subject using a plurality of electrical muscle stimulation electrodes incorporated into a garment that delivers a corresponding plurality of channels of stimulation to the plurality of electrical muscle stimulation electrodes at locations along the circumference of the subject's forearm.

2. The method in claim 1, further comprising capturing EMG muscle motion data from the sensed neuromuscular event associated with tremors experienced by the patient and determining the synthesized pattern based on the captured EMG muscle motion data.

3. The method of claim 1, wherein the synthesized pattern comprises pulses of specific intensity, duration, interval and/or frequency.

4. The method of claim 1, wherein the electrical muscle stimulation in the synthesized pattern is administered to the subject using at least 8 electrical muscle stimulation electrodes incorporated into a garment that delivers at least eight channels of stimulation to locations along the circumference of the subject's forearm.

5. The method of claim 1, comprising determining the synthesized pattern based on pulse segmentation of the EMG muscle motion data, isolating a pulse segment with non-baseline activity, and determining a fundamental frequency, a duration and an intensity of the pulse segment.

6. The method of claim 5, wherein the electrical muscle stimulation in the synthesized pattern is based on an average set of impulse parameters determined from a plurality of pulse segments with non-baseline activity.

\* \* \* \* \*